United States Patent [19]

Krone

[11] 4,388,824
[45] Jun. 21, 1983

[54] PROCESS AND AN APPARATUS FOR TESTING THE COAGULATION PROPERTIES OF LIQUIDS

[76] Inventor: Herbert Krone, Niedernkamp 11, D-4933 Blomberg, Fed. Rep. of Germany

[21] Appl. No.: 238,095

[22] Filed: Feb. 25, 1981

[30] Foreign Application Priority Data

Feb. 29, 1980 [DE] Fed. Rep. of Germany ....... 3007722

[51] Int. Cl.³ ............................................. G01N 33/48
[52] U.S. Cl. ........................................ 73/64.1; 356/39
[58] Field of Search ................... 73/64.1; 356/39, 427; 23/230 B

[56] References Cited

U.S. PATENT DOCUMENTS

| | | | |
|---|---|---|---|
| 3,302,452 | 2/1967 | Leslie | 73/64.1 |
| 3,969,079 | 7/1976 | Catarious et al. | 356/39 X |
| 4,034,601 | 7/1977 | Geiger | 73/64.1 |
| 4,081,242 | 3/1978 | Girolami | 73/64.1 X |

FOREIGN PATENT DOCUMENTS 961221 3/1957 Fed. Rep. of Germany ....... 73/64.1
2160276 6/1972 Fed. Rep. of Germany.

OTHER PUBLICATIONS

"Blutgerinnung Methoden zur Erfassung des Gerinnungseintritts", G-I-T-Fachzeitschrift fuer das Laboratorium, F. P. Grauper.

Primary Examiner—E. R. Kazenske
Assistant Examiner—Joseph W. Roskos
Attorney, Agent, or Firm—Schwartz, Jeffery, Schwaab, Mack, Blumenthal & Koch

[57] ABSTRACT

The coagulometer for measuring the clotting time of liquids such as blood has a turning sample vessel whose axis of turning is at an angle to the vertical. Within the vessel an annular space is formed. The amount of liquid to be tested placed in the annular space is such that no complete ring stretching right the way round the axis of turning is formed when the vessel is not being turned or is being turned before clotting has started. When however clotting takes place sample liquid is transported up the sloping lower face of the annular space, such motion being sensed by a recording system.

16 Claims, 4 Drawing Figures

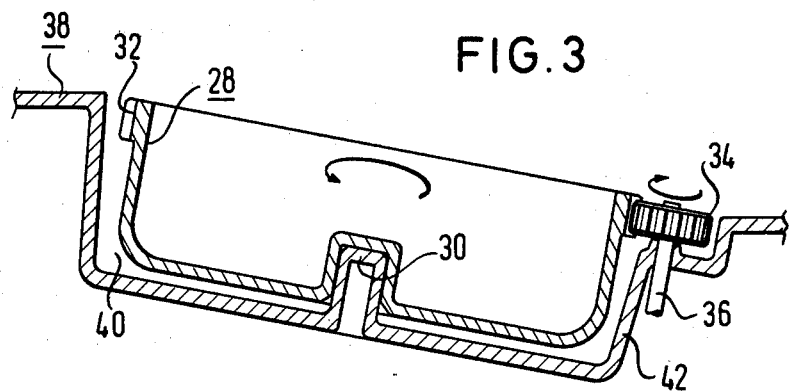
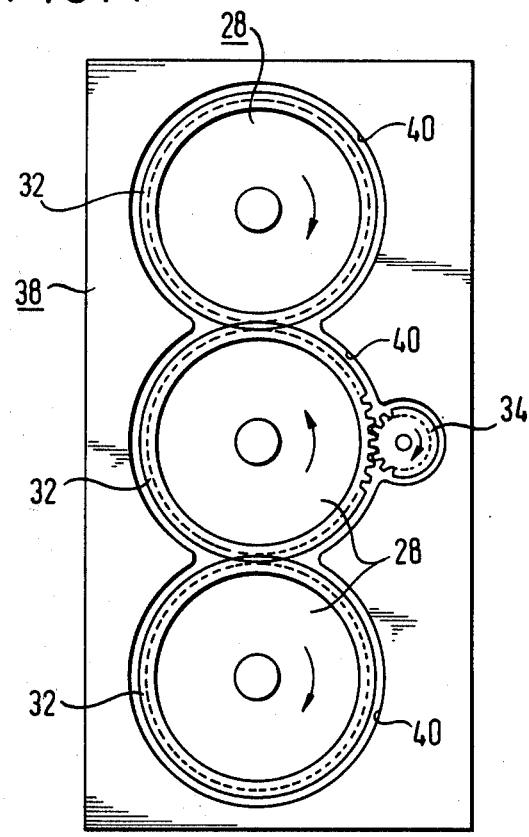

PROCESS AND AN APPARATUS FOR TESTING THE COAGULATION PROPERTIES OF LIQUIDS

BACKGROUND OF THE INVENTION

The present invention is with respect to a process for testing the coagulation properties of a liquid and to a coagulation testing apparatus or coagulometer.

A great number of different ways of measuring the coagulation properties of liquids, as for example blood, or for measuring the time taken before coagulation takes place have been put forward. For a general overview of prior art systems for measuring the clotting properties of blood see, for example, the paper by F. P. Gauper with the title "Blutgerinnung—Methoden zur Erfassung des Gerinnungseintritts" in GIT-Fachzeitschrift für das Laboratorium, 19th year, special issue 1975, pages 509 to 512.

In the last one or two years developments have more specially taken place with the purpose of effecting automatically measuring and recording the clotting or coagulation time. In some of such systems a ball or the like is placed in a measuring vessel, in which the blood is placed and which is turned or moved in some other way and the ball is kept by a force, such as a magnetic field or gravity, in a given position as desired, which is not dependent on the motion of the measuring vessel. At the start of clotting and forming of fibrin, the ball is moved as well by the motion of the measuring vessel because a fibrin structure is formed within the vessel. The point in time, at which the ball is moved out of the position it had in the first place, may be sensed optically, inductively, capacitively etc.

Such systems all have the shortcoming that, in addition to the measuring vessel, which is mostly only designed for use once and then thrown away, it is necessary to have a ball which is normally made with a high degree of accuracy so that it is not possible for it to be thrown away and in fact it has to be carefully cleaned after each measuring operation.

Furthermore, purely optical systems have been put forward in the prior art in which cloudiness produced when clotting takes place is sensed by a photoelectric detector system. Such a system may clearly only be used for testing plasma and not for natural blood.

Further prior art systems have been based on changes in the oscillation properties of a sample at the start of clotting. However such an apparatus has the shortcoming that, because of its high sensitivity, vibrations acting on the apparatus from the outside are likely to have an effect on it.

SHORT OVERVIEW OF THE INVENTION

One purpose of the present invention is that of designing a process and an apparatus of the sort in question, which while being simple, and more specially simple and low in price from the point of view of apparatus design, makes certain of trouble-free measuring of the coagulation time.

For effecting these and other purposes, the liquid whose coagulation property is to be tested, is placed in an annular space in a vessel placed so that the annular space is at an angle to the horizontal. The amount of liquid placed in the vessel is only such as to take up the lower part of the annular space, that is to say without forming a complete ring of liquid. The vessel is then turned about its axis, which is at an angle to the vertical, and the transport of liquid into the higher-up parts of the annular space is sensed.

Such a way of testing may be undertaken free of trouble and with extremely simple apparatus. The "annular space" may simple be formed by a throw-away cup which is turned about a sloping axis, it having such a diameter and being placed at such a slope that the volume of a normal sample will be run into a lower part of the annular space without covering the complete floor or lower face of the space. More specially however the floor of the annular space is not flat but in the form of a groove which is ring-like or part ring-like in radial section so that the face covered by the sample may be more exactly limited. The face walling in the annular space and acted upon by the liquid sample may be made rough, for example by ridges, cuts or the like.

On undertaking the testing operation of the present invention the liquid sample will at the start of testing be kept by gravity in the lower part of the annular space not forming a full ring-like body of liquid within the annular space. At the start of coagulation or clotting however of blood, threads of fibrin will be kept sticking to the wall of the annular space so that the clotted liquid will be transported, on turning of the annular vessel, against the force of gravity in the direction of turning. A detector, which may for example be spaced by 90° from the lowest point in the annular vessel makes it possible for the transport or entrainment of the clotted liquid on turning of the annular vessel to be measured. Such a detector has to be spaced at some distance from the lowest point in the annular vessel because, when the vessel is turned there will be some irregular motion of the edge of the body of liquid even before clotting and it is important that such small irregular motion have no effect on the detector.

The detector or sensing system may, more specially, be a photoelectric detector having a light at one end of a given path and a photoelectric unit at the other end thereof. However it is furthermore possible for capacitive measuring systems of different sorts to be used.

For driving the sample vessel in the desired direction and for the same time housing the detector, the floor of the vessel is more specially at a higher level in its middle part in the form of a hollow headpiece, which may be used on the one hand for fixing the vessel on the driving shaft of a driving system and on the other hand for housing the one end of the detector system.

The sample vessel may for example be made of glass-clear plastics or may be made of glass itself, if desired.

LIST OF FIGURES

An account will now be given of working examples of the coagulometer of the invention using the figures.

FIG. 3 is a view on the same lines as that of FIG. 1, but of a further working example of the invention.

FIG. 4 is a plan view of the structure of FIG. 3.

DETAILED ACCOUNT OF WORKING EXAMPLES OF THE INVENTION

Figure 1:
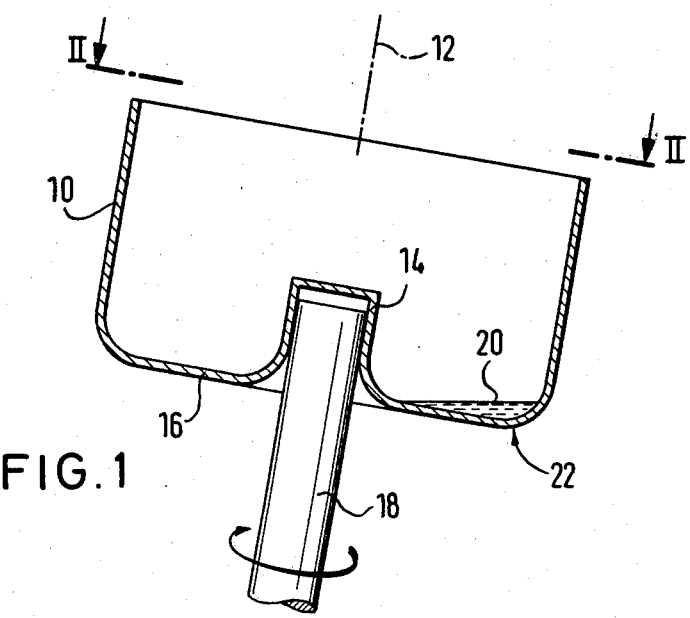
FIG. 1 is a diagrammatic section through part of a coagulometer of the present invention with a sample vessel.

In FIG. 1 a cross-section of a generally cylindrical sample vessel 10 will be seen, whose axis 12 of turning (the axis of the generatrix of the vessel) is at an angle of about 5°–25° to the vertical. In the working example viewed, sample vessel 10 has a hollow headpiece 14 on its bottom or floor 16 which is at such a higher level as it may be used for slipping and fixing the sample vessel 10 on a driving shaft end 18, whose driving system is not given in the figure.

Figure 2:
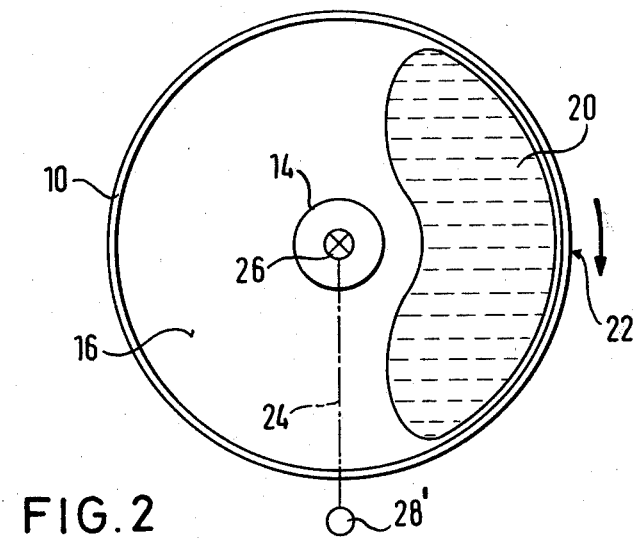
FIG. 2 is a plan view, looking in the direction of arrow 2—2 of FIG. 1.

The diameter of the sample vessel 10 is very much greater than those of test tubes as normally used for such purposes so that, because the axis 12 of turning is at a slope, it is possible for a blood sample 20 to be taken up only in the lower part 22 of the path of turning of the sample vessel 10 without the blood sample covering the full floor 16 of the vessel, that is to say without forming a body in the form of a complete ring. The face or area taken up by the blood sample 20 will be seen more clearly in FIG. 2.

While it is still in a freely flowing condition, the blood sample 20 will be kept by its own weight, that is to say by gravity, in the lower part 22 of the path of turning of the vessel even when the vessel 10 is being turned; clotting of the blood will be the cause of the blood's sticking to the floor 16 so that it will be transported against the effect of gravity on further turning of the sample vessel 10. Once the clotted blood sticking to the vessel floor gets to the level of the beam or path 24 a pulse will be produced which takes effect on the recording and control system of the apparatus, which may be of known design and for this reason is not detailed in connection with the present invention.

If the detector is in the form of a photoelectric detector system using a light beam, one end of the beam, for example a light 26, may be placed and housed within the top end 18 of the shaft, which in this case is hollow, while the photocell 28' at the beam's other end is placed without the sample vessel 10, it then being necessary for at least the end 18 of the shaft to be made transparent or for it to have a window which will then be turned with the rest of the shaft.

Furthermore the sensing operation may be undertaken by a capacitive system placed on the outside of sample vessel 10.

A further possible sensing system may take the form of a unit producing a low frequency or audio frequency vibration for acting on the blood sample 20 in the lower part 22 of the path of turning of the sample vessel. A receiver for such an oscillation may in this case, again, be placed at an angle of about 90° from the unit producing the oscillation. Once the blood has clotted so that it will be sticking to the floor of the sample vessel 10 the low or audio frequency oscillation will be transmitted from the lower part 22 along the blood sticking to the floor as far as the position of the receiver. The receiver and the electronic circuit joined therewith may be so calibrated that not only the start of clotting as such may be sensed and measured but furthermore quantitative figures and readings may be produced for producing a clot curve with respect to time.

Because the vessel is best made as a throw-away cup to keep down prices, a further development may be made as part of the invention which is more specially useful on testing a number of samples at the same time in labs or the like. In this case, in place of the turning shaft end 18, a fixed support pin may be used on which the vessel, placed thereon, may be turned with little friction, because of the form of the outer face of this pin. This further working example of the invention will be seen in FIGS. 3 and 4.

The sample vessel, numbered 28 in this case, is placed on a fixed pin 30, which in this case as well is placed at a small slope to the vertical, the vessel being freely running on this pin. The outer edge of vessel 28 has teeth 32 acted upon by a small gear 34 keyed on a driving shaft 36 coming out from housing 38 and parallel to pin 30.

Housing 38, which is not to be seen in full detail, has a hollow 40 (see FIG. 3) whose form is generally in agreement with the outer form of vessel 28 and within hollow 40 the temperature is controlled by a thermostat as may be necessary for testing the blood sample.

The wall 42 of hollow 40 is let back somewhat on the right hand side (in FIG. 3) for housing the small gear 34 so that the teeth of gear 34 are drivingly lined up with the teeth 32 of vessel 28 for turning the vessel.

Because vessel 28 and its outer teeth 32 take the form of throw-away part, the driving teeth do not have to be made specially accurately, as would be the case for example in gearing designed for a long working life.

The apparatus of FIG. 3 may readily be used for testing a number of samples at the same time without any branching of the gear driving system and in this case it is in fact only necessary to have the desired number of fixed pins 30 in different, joined-together parts of the hollow 40 of housing 38 of FIG. 4. The distances between and the position of the pins 30 will have to be such that the outer teeth 32 on the vessels 28 placed side-by-side will be drivingly acting on each other. Each further vessel is in this case turned by the vessel 28 which in turn is turned by the small gear or pinion 34. The fact that the vessels are turned in different directions may readily be taken into account in placing the sensing systems. Generally speaking, any desired number of vessels may be lined up in such a system and turned at the same time.

A branching driving system with a number of driving output gears and designed for a long working life, would be complex and, in the interests of producing such a long working life, would have to be made with a high degree of accuracy.

I claim:

1. A process for testing a liquid with respect to coagulation thereof, comprising the steps of:
    placing an amount of the liquid to be tested into an annular space within a sample vessel, said annular space being at a slope in relation to the horizontal and having a generatrix axis at an angle to the vertical, the amount of the liquid being sufficient to form a body within a lower part of said annular space stretching partly around said generatrix axis;
    continuously rotating said vessel about said generatrix axis wherein the liquid upon coagulation is transported to a higher part of said annular space; and
    sensing the presence of said coagulated liquid at the higher part of said annular space.

2. The process of testing as claimed in claim 1 wherein said transport of said liquid is optically sensed.

3. The process of testing as claimed in claim 1 wherein said transport of said liquid is capacitively sensed.

4. A process as defined in claim 1, wherein the angle between said generatrix axis and the vertical comprises an acute angle.

5. A process as defined in claim 4, wherein said acute angle ranges from about 5° to 25°.

6. A process as defined in claim 1, wherein said liquid forms a kidney-shaped body in said annular space.

7. An apparatus for testing a liquid with respect to coagulation thereof, comprising:
- an annular vessel at a slope to the horizontal having a generatrix axis at a slope to the vertical;
- a means for continuously rotating said vessel about said generatrix axis; and
- a means for sensing the presence of a coagulated liquid at a higher part of said vessel, wherein said vessel is of a size and at an angle to provide for the transport of said coagulated liquid from a lower part to said higher part of said vessel.

8. The invention of claim 7 wherein said vessel has a generally upwardly turned floor face, in which a groove is formed which is radial section with respect to said axis is ring-like.

9. The invention as claimed in claim 8 wherein said vessel is generally cup-like and has a hollow headpiece in the middle of its floor and forming an inner wall face of said groove.

10. The invention as claimed in claim 7, claim 5 or claim 6 wherein said vessel has a rough inner face for acting on said liquid.

11. The invention as claimed in claim 7, claim 5 or claim 6 in which said axis is at an angle of 5°–25° to the vertical.

12. The invention as claimed in claim 9, further having a driving shaft ending within said headpiece, and a sensing unit within said shaft, said sensing unit forming one end of said sensing means.

13. The invention as claimed in claim 9, further having a ring of gear teeth on the outer face of said vessel.

14. The invention as claimed in claim 7 wherein said sensing means has a unit for producing a beam of oscillations moving along a desired path to a sensing unit, said path being generally in relation to said axis.

15. An apparatus as defined in claim 7, wherein said vessel comprises a raised central floor region through which said generatrix axis passes at an approximately 90° angle to said floor, said raised floor region forming, with the walls of said vessel, said annular space.

16. A method of measuring the clotting time of blood, comprising the steps of:
- placing a liquid blood sample, prior to clotting, onto a sloping support face having a generatrix and generatrix axis, said sample forming a body stretching partly around said axis;
- continuously rotating said face about said axis, wherein said blood sample is transported up said sloping face upon coagulation; and
- sensing the presence of said coagulated blood at a higher point on said sloping face.

* * * * *